United States Patent [19]

Hergenrother et al.

[11] Patent Number: 5,344,982

[45] Date of Patent: Sep. 6, 1994

[54] DIAMINES AND POLYIMIDES CONTAINING PENDENT ETHYNYL GROUPS

[75] Inventors: Paul M. Hergenrother, Yorktown; Brian J. Jensen, Williamsburg, both of Va.

[73] Assignee: The United States of America as represented by the Administrator of the National Aeronautics and Space Administration, Washington, D.C.

[21] Appl. No.: 45,345

[22] Filed: Apr. 2, 1993

[51] Int. Cl.$^5$ .................. C07C 211/54; C07C 211/56
[52] U.S. Cl. .................... 564/330; 564/335; 528/353
[58] Field of Search ................. 564/330, 335

[56] References Cited

U.S. PATENT DOCUMENTS 3,828,071 8/1974 Kast et al. ............... 564/330 X
4,990,667 2/1991 Burgoyne et al. ............ 564/335

OTHER PUBLICATIONS

Jensen et al, Chemical Abstracts, vol. 118 (1993) 213671m.

Primary Examiner—Richard L. Raymond
Attorney, Agent, or Firm—George F. Helfrich

[57] ABSTRACT

Diamines containing pendent ethynyl and substituted ethynyl groups are synthesized. These diamines are reacted with dianhydrides to form polyamide acids, which are chemically or thermally cyclodehydrated to form polyimides and copolyimides with pendent ethynyl groups. Upon heating, the pendent ethynyl groups react to form crosslinked resins that are useful as adhesives, composite matrices, coatings, moldings and films.

4 Claims, 4 Drawing Sheets

DIAMINES AND POLYIMIDES CONTAINING PENDENT ETHYNYL GROUPS

ORIGIN OF THE INVENTION

The invention described herein was made by employees of the United States Government and may be used by or for the Government for governmental purposes without the payment of any royalties thereon or therefor.

BACKGROUND OF THE INVENTION

1. Field of the Invention

The present invention relates generally to condensation polymers. It relates in particular to polyimides containing pendent ethynyl groups. It relates also in particular to diamines containing pendent ethynyl groups, which diamines are used in the preparation of the polyimides containing pendent ethynyl groups.

2. Description of Related Art

Polyimides are condensation polymers that can be prepared by various synthetic routes. The most popular route involves the reaction of an aromatic dianhydride with an aromatic diamine. The intermediate polyamide acid is either thermally or chemically cyclodehydrated to form the polyimide, which has a repeat unit of the general type where Ar is a tetravalent aromatic radical, which can be as simple as a 1,2,4,5-tetrasubstituted benzene. Alternatively, Ar may be a bis-4(1,2-methylenediphenylene) having the general structure where X=nil, O, S, $SO_2$, C=O, etc. Moreover, Ar may be any other appropriate tetravalent radical. Ar' is a divalent aromatic radical which may be 1,3=phenylene, 1,4-phenylene, 4,4'-oxydiphenylene, 4,4'-biphenylene, 4,4'-thiodiphenylene, 4,4'-carbonyldiphenylene, diphenylimethane or any other appropriate divalent radical.

Synthesis and characterization of polyimides has been extensively reported in the literature. The preparation of aromatic polyimides by reaction of an aromatic dianhydride with an aromatic diamine, followed by thermal cyclization was first reported in 1963 (G. M. Bower and L. W. Frost, *J. Polym. Sci. A*1, 3134 (1963)) with patents awarded in 1965 (W. M. Edwards, U.S. Pat. Nos. 3,179,614 and 3,179,634 and A. L. Endrey, U.S. Pat. Nos. 2,1796,631 and 3,179,633). Several reviews on polyimides have been published (C. E. Sroog, "Polyimides" in *Encycl. of Polymr. Sci. and Tech.* [H. F. Mark, N. G. Gaylord and N. M. Bikales, ed.] Interscience Pub., New York, 1969, Vol. 11, pp. 247-272; N. A. Adrova, M. I. Bessonov, L. A. Lauis and A. P. Rudakov, Polyimides, Technomic Pub. Co., Inc., Stamford, Conn., 1970).

Wholly aromatic polyimides are known for their exceptional thermal, thermooxididative and chemical resistance, but are generally difficult to process as structural adhesives or composite matrices. Several polyimides such as Kapton ® (DuPont), PI-2080 (Dow Chemical), XU-218 (Ciba-Geigy), Ultem ® (General Electric) and LaRC ™-TPI (Mitsui Toatsu) are commercially available and used as films, moldings, adhesives or composite matrices.

The incorporation of ethynyl groups in polyimides has been reported in the literature, typically as terminal groups to yield acetylene-terminated imide oligomers (ATI). Therimid-600, an oligomide with acetylenic end groups, was first developed at the Hughes Aircraft Co. [N. Bilow, A. L. Landis and L. J. Miler, U.S. Pat. No. 3,845,018 (1974); A. L. Landis, N. Bilow, R. H. Boschan, R. E. Lawrence and T. J. Aponyi, *Polym. Prepr.*, 15, 537 (1974); N. Bilow and A. L. Landis, Natl. SAMPE Tech. Conf. Ser., 8,94 (1976)]. Several reviews on polyimides or acetylene-terminated prepolymers are published which discuss other acetylene containing polyimides [P. M. Hergenrother (H. Mark, ed.), *Encycl. Polym. Sci. and Eng.*, 2nd. ed., Vol. 1, John Wiley and Sons, Inc., New York, 61 (1985); P. M. Hergenrother (H. Mark, ed.) *Encycl. Polym Sci. and Eng.*, 2nd ed., Vol. 7, John Wiley and Sons, Inc., New York, 639 (1987); T. Takekoshi (C. G. Overberger, ed.) *Advances in Polymer Sci.*, 2 (1990)]. Polyimides containing pendent ethynyl groups has been reported [F. W. Harris, S. M. Podaki and S. Varaprath, *Polym. Prepr.*, 21 (1), 3 (1980)]. This reference contains an abstract only, no experimental details or polymer properties being reported.

SUMMARY OF THE INVENTION

An object of this invention is to provide diamines containing a pendent ethynyl group.

Another object of this invention is to provide diamines containing a pendent phenylethynyl group.

Another object of this invention is to provide diamines containing a pendent substituted ethynyl group.

Another object is to provide diamines which initiate a crosslinking reaction at temperatures about 150° C. to about 400° C.

Another object is to provide poly(amic acids) with pendent ethynyl or substituted ethynyl groups from the reaction of the above diamines with dianhydrides.

Another object is to provide polyimides with pendent ethynyl or substituted ethynyl groups by cyclodehydrating the above poly(amic acids).

Another object is to provide polyimides which crosslink to form a network structure by heating at elevated temperatures.

Another object is to provide copolymers which crosslink to form a network structure by heating at elevated temperatures.

These objects and the attending benefits are achieved according to the present invention by first providing a series of diamines having the general structural formula:

where R=H, C₄H₉, etc. and R'=CH₃ or CF₃.

These diamines contain an ethynyl or substituted ethynyl group which undergoes a thermal reaction with other ethynyl groups at temperatures from about 150° C. to about 400° C., depending on the R group. In comparing the curing behavior of two different materials: when R=H, differential scanning calorimetry at a heating rate of 20° C./minute indicates that the reaction is initiated at about 225° C. and is complete after one-half hour at 250° C. However, if R=φ, the reaction initiates at slightly less than 350° C., and is complete after a short period (< one hour) at 350° C. Materials with other R groups would be expected to have different reaction initiation temperatures. The amine functionality can react with anhydrides to form amic acids, or it can react with acids and acid chlorides to form amides. Since these amines are difunctional, they can react with other difunctional compounds to form polymers.

Polyamide acids are initially prepared from the reaction of the ethynyl containing diamines with dianhydrides. Subsequent cyclodehydration by heating or by chemical methods produces polyimides containing pendent ethynyl or substituted ethynyl groups. Upon heating these polymers at elevated temperatures, the ethynyl groups react with one another to form a crosslink structure. As a result of this curing reaction, the solvent resistance, glass transition temperature, and modulus of the polymers generally increase, accompanied by a corresponding decrease in tensile elongation and toughness. These cured polymers can be used as films, coatings, moldings, adhesives, and composite matrices.

The advantage of polyimides containing pendent ethynyl groups compared to linear polyimide is their ability to react to form a crosslink structure which typically has an increased solvent resistance, and higher glass transition temperature and modulus. These properties are important for electronic and aerospace applications such as films, coatings, moldings, adhesives and composites.

The advantage of polyimides containing pendent ethynyl groups compared to acetylene-terminated imide oligomers (ATI) is that the polyimides containing pendent ethynyl groups have a high molecular weight and form tough films before the ethynyl crosslinking reaction takes place. The ATIs typically form brittle films. Furthermore, the crosslink density of the cured resins from polyimides containing pendent ethynyl groups can be controlled by copolymerizing a diamine without ethynyl groups and a diamine containing pendent ethynyl groups to form high molecular weight polymers. With ATIs, the crosslink density can be varied only by changing the molecular weight of the oligomer, which affects the ability to make films and moldings.

BRIEF DESCRIPTION OF THE DRAWINGS

For a more complete understanding of the present invention, including its objects and attending benefits, reference should be made to the Description of the Preferred Embodiments, which is set forth below. This Description should be read together with the accompanying drawings wherein.

DESCRIPTION OF THE PREFERRED EMBODIMENTS

A series of novel diamines containing pendent ethynyl groups or substituted ethynyl groups were synthesized. See FIGS. 1 and 2 for the reaction schemes employed. The resulting diamines were then reacted with various dianhydrides to form polyamide acids, which were cyclodehydrated to form polyimides containing pendent ethynyl groups or substituted ethynyl groups. See FIG. 3 for a schematic of the reaction employed. Finally, copolyimides from the diamines containing pendent ethynyl or substituted ethynyl groups and other diamines were also prepared. See FIG. 4 for the reaction scheme employed. The polyimides so produced were characterized (see Table 1 below), as were the copolyimides (see Table 2 below). Mechanical properties of films prepared from the polymers and copolymers were determined, and the thermal stability and film properties of the copolymers were tabulated (see Table 3 below). Specific examples, which are for purposes of illustration only are presented as follows.

EXAMPLE 1

Figure 1:
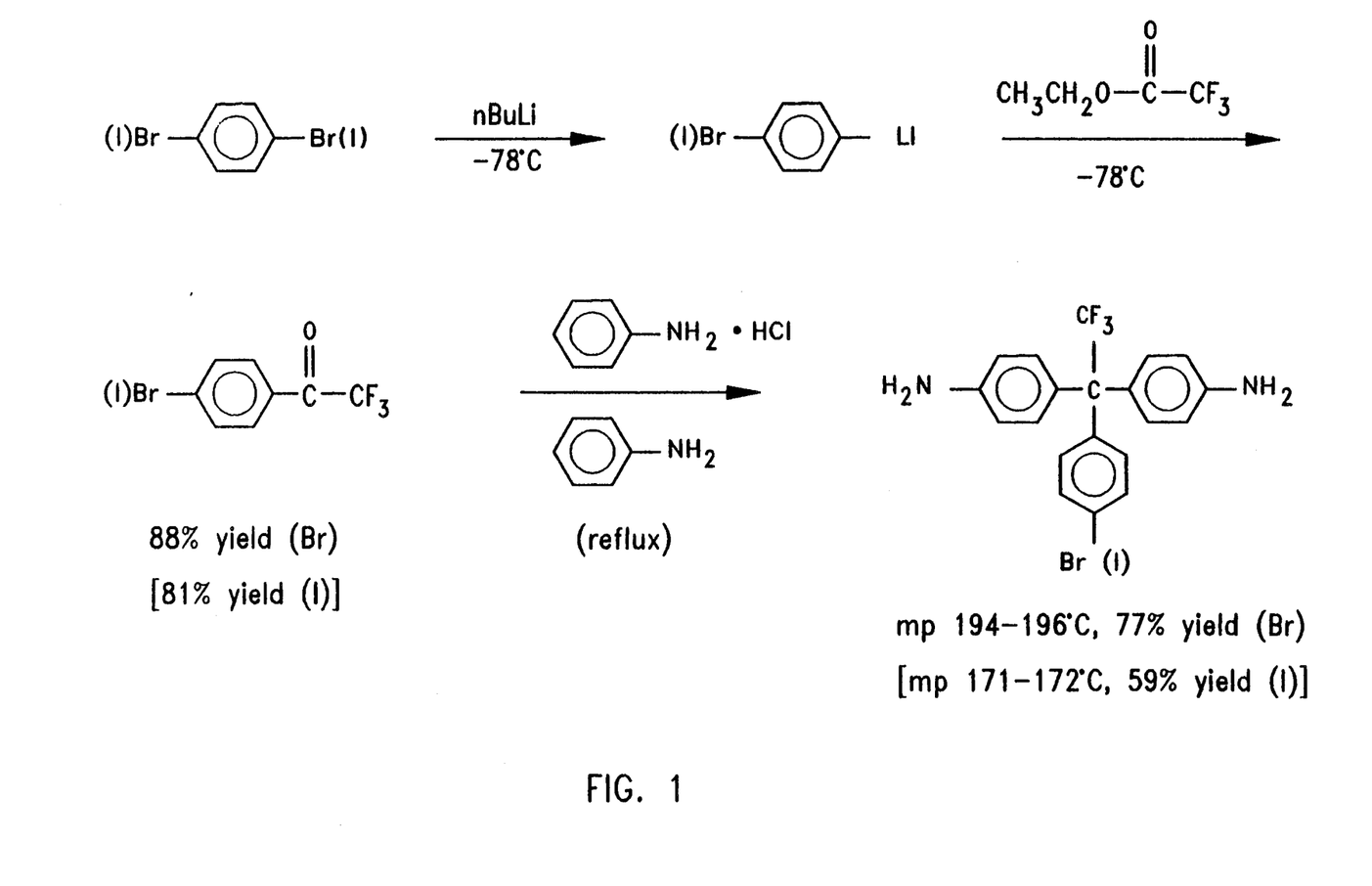
FIG. 1 is a representation of the reaction scheme for the preliminary stages of a process for preparing novel diamines containing pendent ethynyl groups or substituted ethynyl groups according to the present invention.

Synthesis of 4-bromotrifluoroacetophenone (see FIG. 1)

Into a flame-dried three-necked round bottomed flask, fitted with a pressure equalizing addition funnel and under nitrogen was added 1,4-dibromobenzene (20.04 g, 84.00 mmol). Using a syringe, 150 mL of anhydrous ether was added into the flask. Some of the 1,4-dibromobenzene dropped out of solution when the solution was cooled to −78° C. in a dry-ice/acetone bath. An amount of n-butyl lithium (m-BuLi) (1.6M in hexane, 55 mL; 88 mmol) was introduced into the addition funnel with a syringe, and the funnel was adjusted for dropwise addition of the n-BuLi solution into the reaction flask. The addition was completed in 30 minutes, and the resulting white suspension was stirred at −78° C. for two hours. After two hours, the reaction vessel was removed from the bath and allowed to warm to 0° C. to ensure complete metal-halogen exchange. The reaction mixture changed from a suspension to a solution on warming. On recooling to −78° C., the suspension reappeared. To this white suspension was added dropwise, through the addition funnel, 13.47 g (95.00 mmol) of ethyl trifluoroacetate. The suspension became a solution before complete addition of the ester and the solution was left to warm to room temperature in about 12 hours.

To quench the reaction, the solution was cooled to between −30° C. and −20° C., and then 40 mL of aqueous saturated ammonium chloride ($NH_4Cl$) was added dropwise through the addition funnel. To ensure complete hydrolysis, 40 mL of 1N hydrochloric acid (HCl) was added and the mixture was allowed to warm up to room temperature. The reaction mixture was transferred to a separatory funnel and the aqueous layer was run off. The ether solution was washed carefully with saturated aqueous sodium bicarbonate ($NaHCO_3$), until all the acid was neutralized (no effervescence on adding fresh amounts of the aqueous bicarbonate). The ether solution was transferred to a flask and dried over anhydrous magnesium sulfate ($MgSO_4$). Suction filtration, followed by rotary evaporation of the solvent, left a yellow-colored, slightly lacrimatory liquid which was vacuum distilled (0.2 Torr, 80° C.) to obtain 19.75 g(88%) of 4-bromotrifluoroacetophenone as a dense, colorless liquid. The liquid solidified on storing in the refrigerator. $^1H$ NMR: an AB quartet centered at 7.66 ppm.

4-Iodotrifluoroacetophenone[2] was prepared by a similar procedure in 81% yield from p-diiodobenzene. $^1H$ NMR: an AB quartet centered at 7.65 ppm.

EXAMPLE 2

Synthesis of 1,1-bis(4-aminophenyl)-1-(4-bromophenyl)-2,2,2-trifluorethane (See FIG. 1)

4-Bromotrifluoracetophenone (33.53 g, 132 mmol) was placed in a 500 mL single-necked round bottomed flask followed by 23 g (178 mmol) of purified aniline hydrochloride. After freshly distilled aniline (93 mL) was added, the flask was fitted with a reflux condenser connected to a nitrogen line. The reaction mixture was heated to reflux with a heating mantle and maintained at reflux for 24 hours. On cooling to room temperature, 30 g (300 mmol) of solid $NaHCO_3$ was carefully added in portions to neutralize aniline hydrochloride, and the reaction mixture was steam-distilled until the distillate was clear. A dark solid mass and water was left in the flask after it cooled down to room temperature. Water was decanted off, the solid was dissolved in chloroform, and the solution was dried over anhydrous $MgSO_4$. After suction filtration, the dark purple solution was concentrated on a rotary evaporator. The resulting dark purple solid was column chromatographed on silica gel using benzene as eluent [carbon tetrachloride ($CCl_4$) elution, followed by 20% ether in $CCl_4$ also worked, but benzene gave better separation]. A total of 43.18 g (77%) of product was collected as a solid with a light purple color. Analytical samples were prepared by multiple recrystallizations from benzene: mp 194°–6° C.; $^1H$ NMR: δ3.60 (br s, 4H); 6.35–7.30 (two AB quartets, 12H); Mass Spectrum m/e (relative intensity) 422 (M++2,20) 420 (M+,20), 353 (100), 351 (100); Calc'd for $C_{20}H_{16}BrF_3N_2$: C, 57.02; H, 3.83. Found: C, 57.40; H, 3.86.

1,1-Bis(4-aminophenyl)-1-(4-iodophenyl)-2,2,2-trifluoroethane was prepared in a similar manner in 59% yield from 4-iodotrifluoroacetophenone: mp 171°–2° C. (after vacuum heat-drying); $^1H$ NMR: δ3.50 (br s, 4H), 6.44 (d, 4H), 6.80 (d,6H), 7.46 (d,2H): Mass Spectrum, m/e (relative intensity) 468 (M+,40), 399 (100), 272 (20); Calc'd for $C_{20}H_{16}IF_3N_2$: C, 51.30; H, 3.44; N, 5.98. Found: C=51.40; H=3.36; N=5.97.

EXAMPLE 3

Figure 2:
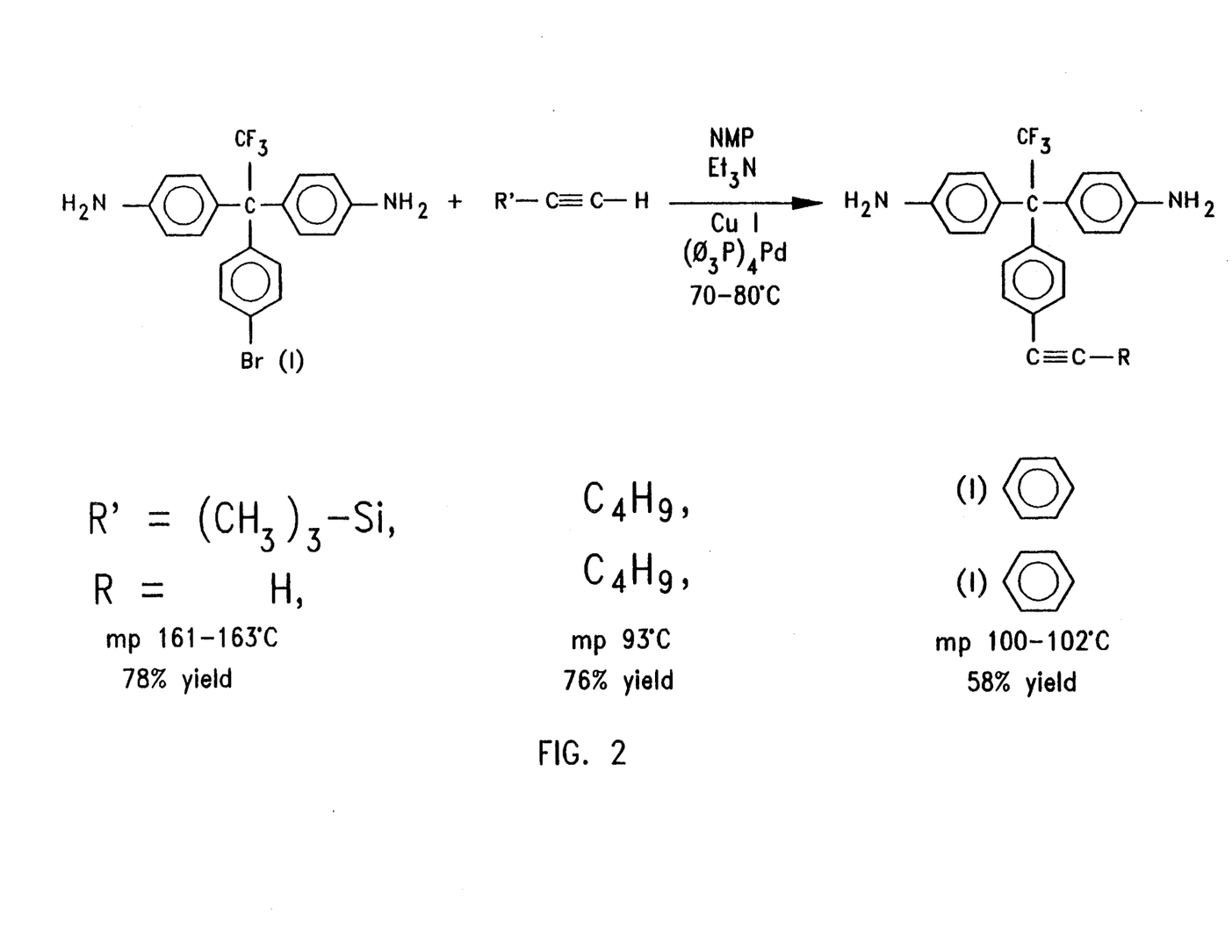
FIG. 2 is a representation of the reaction scheme for the final stage of a process for preparing novel diamines containing pendent ethynyl groups or substituted ethynyl groups according to the present invention.

Synthesis of 1,1-bis(4-aminophenyl)-1-(4-ethynylphenyl)-2,2,2-trifluorethane (See FIG. 2)

1,1-Bis(4-aminophenyl)-1-(4-bromophenyl)-2,2,2-trifluorethane (15.17 g, 35.95 mmol) was dissolved in a mixture of 60 mL of triethylamine and 20 mL of N-methylpyrrolidinone. Copper (I) iodide (0.16 g, 0.84 mmol, 2.3mol %) and tetrakis(triphenylphosphine)palladium (O) (1.00 g, 0.86 mmol, 2.4 tool%) were added, followed by 7.00 g (71.43 mmol) of trimethylsilylacetylene. The solution was sealed in the flask with a rubber septum additionally secured from slipping under pressure with copper wire. The magnetically stirred mixture was heated at 80° C. using an oil bath for 24 hours.

After the reaction, the solvent mixture was removed on a rotary evaporator, the residue was extracted with ether, and the suspension was suction-filtered. The ether extract was washed with water and then dried over anhydrous $MgSO_4$. Suction filtration, followed by rotary evaporation of the solvent left 20.87 g of crude 1,1-bis(4-aminophenyl)-1-(4-trimethylsilylethynyl-phenyl)-2,2,2-trifluoroethane. This crude material was dissolved in 100 mL of methanol, and 6.60 g (61 mmol) of $Na_2CO_3$ was added for resilylation. The flask was stoppered and stirred at room temperature for 24 hours. After filtering off all solids, methanol was removed by rotary evaporation. The residue was extracted with ether to remove any inorganic substances that might have dissolved in methanol. Aqueous wash of the ether solution, followed by drying with anhydrous $MgSO_4$, suction filtration and rotary evaporation, left 16.12 g of crude monomer. Purification was effected by column chromatography with silica gel. Initial slow elution with benzene removed faster eluting impurities. The solvent was then changed to a 50/50 (v/v) mixture of ether and benzene to elute the product. Rotary evaporation of the eluent left a brown viscous oil which on placing on a vacuum pump for three days, foamed up into a yellow voluminous solid. $^1H$ NMR of this solid showed that some benzene was still occluded in the product. To remove the benzene, the product was vacuum heat-dried at 80° C. for about 30 minutes. On cooling to room temperature, a brittle orange glass was left which was ground, giving the monomer as a yellow powder weighing 10.37 g (78%). Analytical samples were prepared by recrystallization from deuterated chloroform ($CDCl_3$): mp 161°–3° C., $^1H$ NMR: δ2.88 (s, 1H), 3.42 (br s, 4H), 6.20–7.08 (m, 12H); Mass Spectrum, m/e (relative intensity): 366 (M+, 25); 297 (100); Calc'd for $C_{22}H_{17}F_3N_2$: C, 72.12; H, 4.68; N, 7.65. Found: C, 72.34; H, 4.79; N, 7.45.

EXAMPLE 4

Synthesis of 1,1-bis(4-aminophenyl)-1-(4-phenylethynylphenyl)-2,2,2-trifluoroethane (see FIG. 2)

Into a single-necked round bottom flask were added 6.27 g (13.39 mmol) of 1,1-bis(4-aminophenyl)-1-(4-iodophenyl)-2,2,2-trifluoroethane, 0.52 g (0.45 mmol; 3.36 mol %) of tetrakis(triphenylphosphine)palladium (O), and 0.11 g (0.58 mmol; 4.3 mol %) of CuI. After the addition of 24 mL of triethylamine and 8 mL of N-methylpyrrolidinone, 2.80 g (27.45 mmol) of phenylacetylene was introduced into the flask. A reflux condenser, connected to a nitrogen line, was attached to the flask and the stirred mixture was maintained at 70° C. with an oil bath for three days. The solvent mixture was removed on a rotary evaporator and the dark red oily residue was extracted with ether continuously until further extraction with fresh ether gave a colorless organic layer. All the ether extracts were collected, washed with water and dried over anhydrous MgSO$_4$. Suction filtration and solution concentration on the rotary evaporator gave a dark-red oil which foamed up to give a fluffy yellow solid on leaving on the evaporator for two-three hours.

The crude product was applied onto a column of silica gel and eluted initially with benzene. After the faster moving components of the crude mixture had eluted (this fraction was a dark red oil), elution was continued with a 9:1 (v/v) mixture of benzene and ether respectively. The product was obtained from this fraction, on rotary evaporation of the solvent and leaving the residue for three hours at 53° C., as a bright yellow foamy solid weighing 3.45 g *58%). $^1$H NMR spectrum of this product indicated that some occluded benzene was still left in the solid. The product was therefore subjected to vacuum heat-drying at 80° C. for 30 minutes. An orange glass was left on cooling to room temperature, which was ground into a yellow powder; top: the compound started to shrink at 85° C., became a glassy ball at 90°-2° C. and melted into an orange liquid at 100-2° C.; $^1$H NMR: δ3.66 (br s, 4H); 6.36-7.36 (m, 17H); Mass Spectrum, m/e (relative intensity); 442 (M$^+$,30), 373 (100); Calc'd for C$_{28}$H$_{21}$F$_3$N$_2$: C, 76.00; H, 4.78; N, 6.33. Found: C, 75.63; H, 4.95; N, 6.15.

EXAMPLE 5

Synthesis of 1,1-Bis(4-aminophenyl)-1-(4-hexynylphenyl)-2,2,2,-trifluoroethane (See FIG. 2)

This compound was prepared in 76% yield from 1,1-(4-aminophenyl)-1-(4-bromophenyl)-2,2,2-trifluoroethane and 1-hexyne by the same procedure as for the phenylethynylphenyl analog. Mp: the compound started to soften and shrink at 53° C., becomes a transparent mass at 62° C. and melted at 93° C. $^1$H NMR: δ0.90 (unresolved, 3H); 1.50 (unresolved, 4H); 2.32 (unresolved, 2H); 3.42 (br s, 4H); 6.55 (AB q, 8H), 7.02 (AB q, 4H), 7.02 (AB q, 4H); Mass Spectrum, m/e (relative intensity) 422 (M$^+$, 20), 353 (100); Calc'd for C$_{36}$H$_{25}$F$_3$N$_3$: C, 73.93; H, 5.96; N, 6.63. Found: C, 74.29; H, 6.13; N, 6.63.

The corresponding 1,1-bis(4-aminophenyl)-1-(4-ethynylphenyl, phenylethynylphenyl and 4-hexynylphenyl) can be prepared through the same procedure by starting with acetophenone in place of trifluoroacetophenone.

Figure 3:
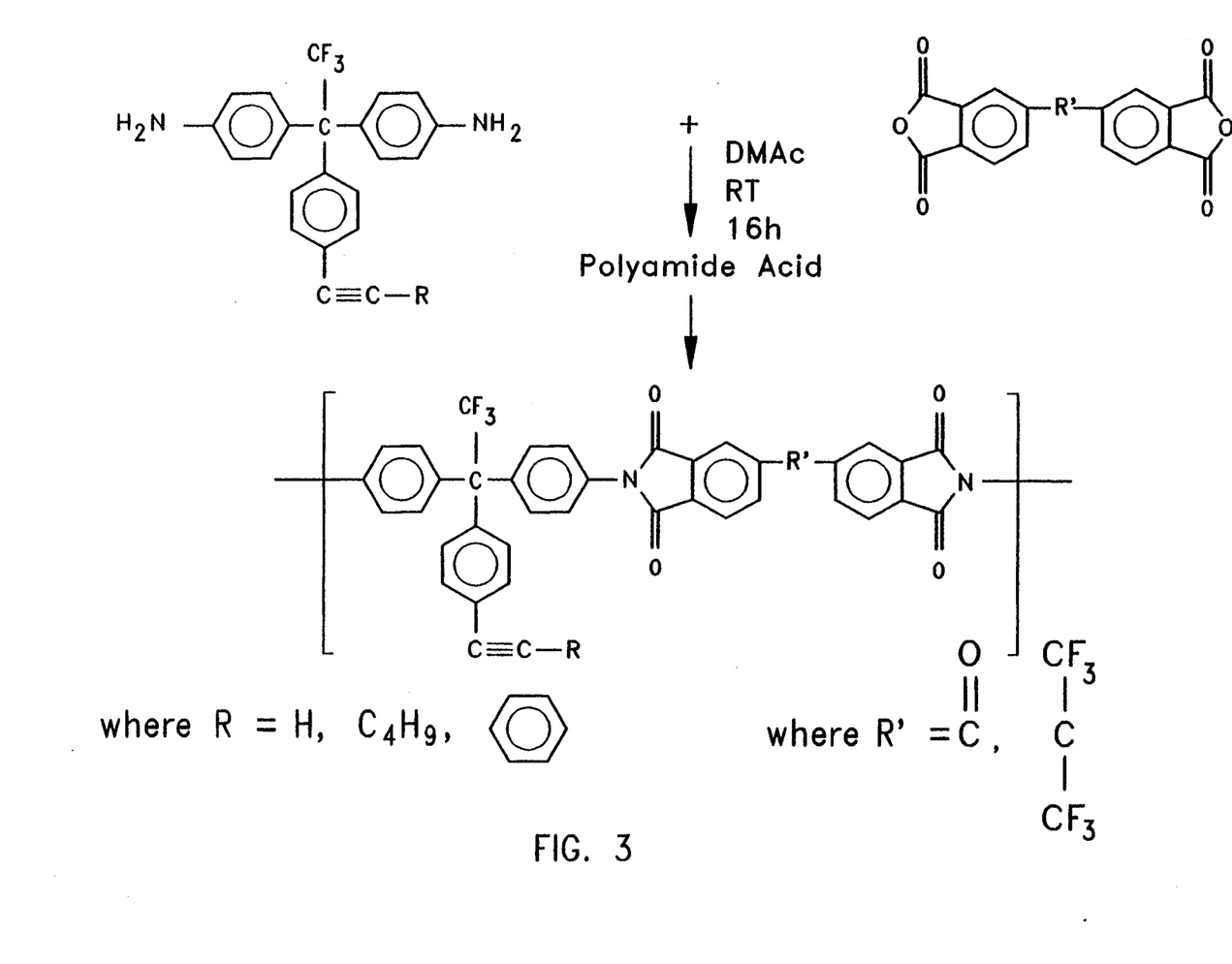
FIG. 3 is a representation of the reaction scheme for preparing polyimides containing pendent ethynyl groups or substituted ethynyl groups according to the present invention.

Synthesis of Polymers. FIG. 3 shows the synthesis of polyimides containing pendent ethynyl or substituted ethynyl groups. Table 1 shows the inherent viscosities ($\eta_{inh}$) of six polyamide acids prepared using diamines containing pendent ethynyl groups. Specific examples of these polymers follow.

EXAMPLE 6

The following example illustrates the synthesis of polyimides with pendent substituted ethynyl groups. 1,1-Bis(4-aminophenyl)-1-(4-phenylethynylphenyl)-2,2,2-trifluorethane (0.005 m, 2.2323 g), 3,3',4,4'-benzophenone tetracarboxylic dianhydride (BTDA) (0.005 m, 1.6112 g) and N,N-dimethylacetamide (DMAc) (21.7 g) were added to a three-neck flask equipped with a stirring motor and nitrogen purge. The reaction was stirred for eight hours at RT to form a polyamide acid with $\eta_{inh}$=0.56 dL/g. This solution was cast onto plate glass and cured in air for one hour each at 100°, 200° and 350° C. to form a crosslink yellow polyimide film with no T$_g$ detected by differential scanning calorimetry (DC) at a heating rate of 20° C./min. This film was completely insoluble in either DMAc or chloroform.

EXAMPLE 7

The following example illustrates the synthesis of polyimides with pendent ethynyl groups. 1,1-Bis(4-aminophenyl)-1-(4-ethynylphenyl)-2,2,2-trifluorethane (0.0025 m, 0.9160 g), 2,2-bis(3,4-dicarboxyphenyl)hexafluoropropane (6FDA) (0.0025 m, 1.1106 g) and DMAc (11.5 g) were added to a three neck flask equipped with a stirring motor and nitrogen purge. The reaction was stirred for eight hours at RT to form a polyimide acid with $\eta_{inh}$=0.80 dL/g. This solution was cast onto plate glass and cured in air for one hour each at 100°, 200° and 300° C. to form a crosslink yellow polyimide film with no T$_g$ detected by DSC. This film was completely insoluble in either DMAc or chloroform.

EXAMPLE 8

The following illustrates the synthesis of polyimides with pendent substituted ethynyl groups. 1,1-Bis(4-aminophenyl)-1-(4-hexynylphenyl)-2,2,2-trifluoroethane (0.0025 m, 1.0562 g), BTDA (0.0025 m, 0.8056 g) and DMAc (10.6 g) were added to a three-neck flask equipped with a stirring motor and nitrogen purge. The reaction was stirred for eight hours at RT to form a polyamide acid with $\eta_{inh}$=0.40 dL/g. This solution was cast onto plate glass and cured in air one hour each at 100°, 200° and 300° C. to form a crosslink polyimide film with no T$_g$ detected by DSC. This film was completely insoluble in either DMAc or chloroform.

Synthesis of Copolymers

Figure 4:
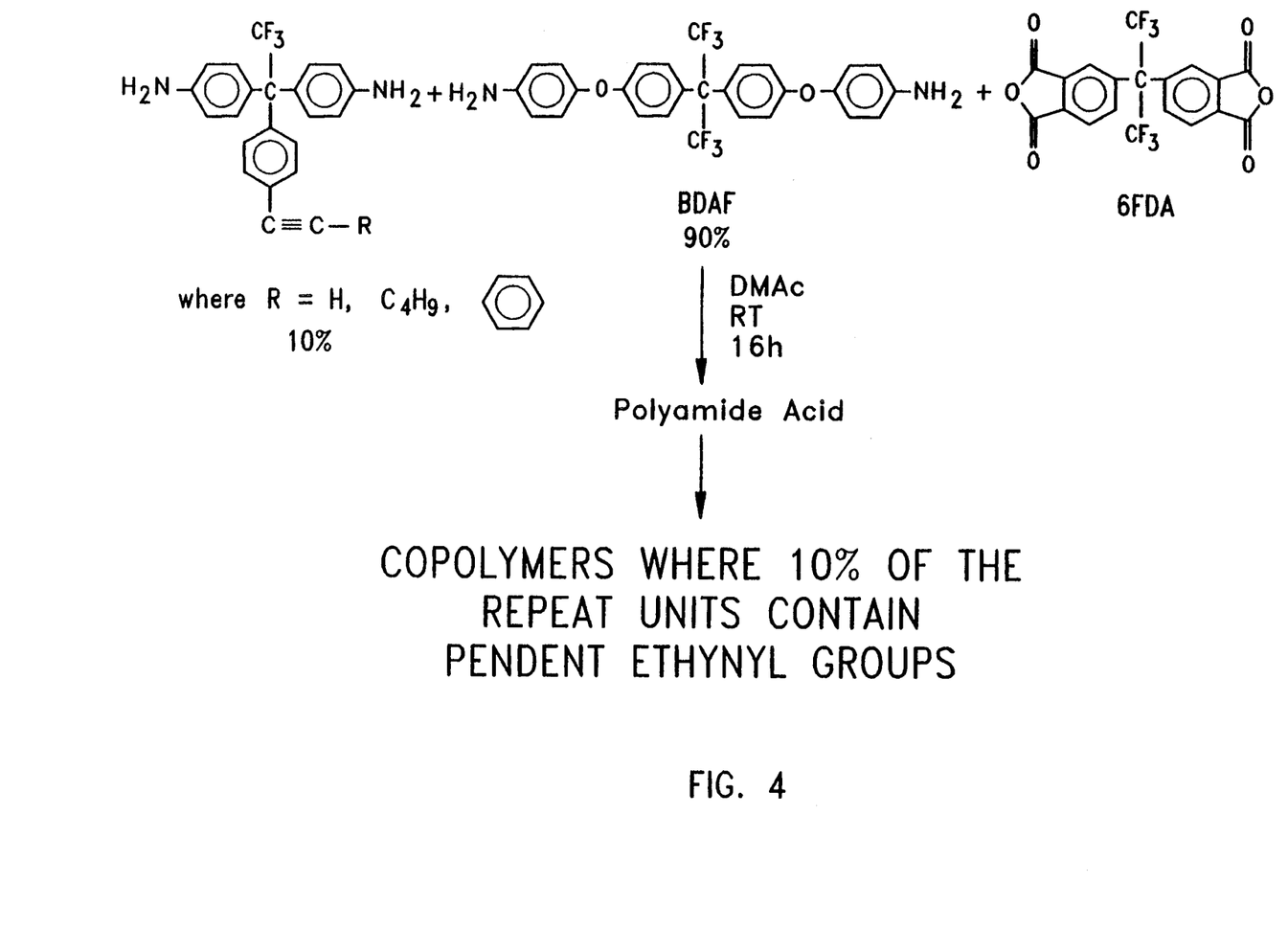
FIG. 4 is a representation of the reaction scheme for preparing imide copolymers containing pendent ethynyl groups or substituted ethynyl groups according to the present invention.

FIG. 4 shows the synthesis of imide copolymers containing pendent ethynyl or substituted ethynyl groups. These copolymers were prepared using 10 mole percent of the diamine that contains the pendent ethynyl group, although any percentage of this diamine could be used. Table 2 gives the $\eta_{inh}$s of the amid acid copolymers and the original and final T$_g$s of the imide copolymers. Table 3 gives data on the thermal stability and film properties (tensile strength, modulus and elongation) of the same copolymers. For reference, the homopolymer of 2,2-bis(4-aminophenoxy-4'-phenyl)hexafluoropropane (BDAF) and 4,4'-hexafluoroisopropylidonediphthalic anhydride (6FDA) has tensile strength, tensile modulus and elongation of 15.6 ksi, 433 ksi and 26.7%, respectively, and the film is soluble in DMAc and CHCl₃. When these copolymers are solution imidized, by collecting a toluene/water azeotropic mixture at 160° C. during 16 hours, the copolymers remain soluble in DMAc. When cured at 250°–350° C., the ethynyl groups react, and the copolymers become insoluble in DMAc. Specific examples of these copolymers follow.

EXAMPLE 9

The following example illustrates the synthesis of an imide copolymer where 10 mole percent of the diamine used contains pendent ethynyl groups. 1,1-Bis(4-aminophenyl)-1-(4-ethynylphenyl)-2,2,2-trifluoroethane (0.001 m, 0.3664 g), 2,2-bis(4-aminophenoxy-4'-phenyl)-hexafluoropropane (BDAF) (0.009 m, 4.6662 g), 4,4'-hexafluoroisopropylidinediphthalic anhydride (6FDA) (0.01 m, 4.4425 g) and DMAc (53.5 g) were added to a three neck flask equipped with a stirring motor and nitrogen purge. The reaction was stirred for eight hours at RT to form a polyamide acid with $\eta_{inh}$=1.54 dL/g. This solution was cast onto plate glass and cured in air for one hour each at 100°, 200° and 300° C. to form a creasible, lightly crosslinked imide copolymer film with $T_g$=275° C. by DSC. This film was completely insoluble in DMAc or chloroform but did swell.

EXAMPLE 10

The following example illustrates the synthesis of an imide copolymer where 10 mole percent of the diamine used contains pendent phenylethynyl groups. 1,1-Bis(4-aminophenyl)-1-(4-phenylethynyl)-2,2,2-trifluoroethane (0.001 m, 0.4425 g), BDAF (0.009 m, 4.6662 g), 6FDA (0.01 m, 4.4425 g) and DMAc (54.1 g) were added to a three neck flask equipped with a stirring motor and nitrogen purge. The reaction was stirred for eight hours at RT to form a polyamide acid with $\eta_{inh}$=1.47 dL/g. This solution was cast onto plate glass and curved in air for one hour each at 100°, 200° and 350° C. to form a creasible, lightly crosslinked yellow imide copolymer film with $T_g$=273° C. by DSC. This film was completely insoluble in DMAc or chloroform but did swell.

EXAMPLE 11

The following example illustrates the synthesis of an imide copolymer where 10 mole percent of the diamine used contains pendent hexynyl groups. 1,1-Bis(4-aminophenyl)-1-(4-hexynylphenyl)-2,2,2-trifluorothane (0.001 m, 0.4425 g), BDAF (0.009 m, 4.6662 g), 6FDA (0.01 m, 4.4425 g) and DMAc (54.0 g) were added to a three neck flask equipped with a stirring motor and nitrogen purge. The reaction was stirred for eight hours at RT to form a polyamide acid with $\eta_{inh}$=1.08 dL/g. This solution was cast onto plate glass and curved in air for one hour each at 100°, 200° and 300° C. to form a creasible, lightly crosslinked yellow imide copolymer film with $T_g$=269° C. by DSC. This film was completely insoluble in DMAc or chloroform but did swell.

TABLE 1

CHARACTERIZATION OF POLYMERS

| Polymer R = | R' = | Polyamide Acid $\eta_{inh}$, dL/g[a] |
|---|---|---|
| H | CO | 0.94 |
| H | C(CF₃)₂ | 0.80 |
| C₆H₅ | CO | 0.77 |
| C₆H₅ | C(CF₃)₂ | 0.68 |
| C₄H₉ | CO | 0.40 |
| C₄H₉ | C(CF₃)₂ | 0.26 |

[a]DMAc at 25° C. and 0.5% concentration.
Note: No Tgs were detected by DSC for the polyimides.

TABLE 2

CHARACTERIZATION OF COPOLYMERS where 90 mole % of Ar = BDAF and 10 mole % of Ar =

| Copolymer R = | Polyamide Acid $\eta_{inh}$, dL/g[a] | DSC Tg, °C.[b] Original[c] | Final[d] |
|---|---|---|---|
| H | 1.54 | 265 | 275 |
| C₆H₅ | 1.47 | 265 | 273 |

TABLE 2-continued

CHARACTERIZATION OF COPOLYMERS

| | C$_4$H$_9$ | 1.08 | 264 | 269 |
|---|---|---|---|---|

[a]DMAc at 25° C. and 0.5% concentration.
[b]DSC at a heating rate of 20° C./min.
[c]Chemically imidized, acetic anhydride and triethylamine.
[d]After heating to 400° C.

TABLE 3

THERMAL STABILITY AND FILM PROPERTIES OF COPOLYMERS where 90 mole % of Ar = BDAF and 10 mole % of Ar =

| | TGA[a] | | | |
|---|---|---|---|---|
| | 5% Weight | | Tensile | Tensile |

TABLE 3-continued

THERMAL STABILITY AND FILM PROPERTIES OF COPOLYMERS

| Copolymer | Loss, °C. | | Strength, | Modulus, | Elongation |
|---|---|---|---|---|---|
| R = | Air | N$_2$ | Ksi | Ksi | % |
| H | 468 | 493 | 14.8[b] | 416[b] | 6.7[b] |
| C$_6$H$_5$ | 450 | 493 | 17.7[c] | 518[c] | 6.1[c] |
| C$_4$H$_9$ | 401 | 493 | 17.8[b] | 534[b] | 5.9[b] |

[a]TGA at a heating rate of 2.5° C./min in flowing atmosphere, 15 ml/min.
[b]Cured at 300° C. in air for 1 hr.
[c]Cured at 350° C. in air for 1 hr.

We claim:
1. A diamine having a pendent ethynyl or substituted ethynyl group and having the following structural formula:

wherein R is a member selected from the group consisting of hydrogen, alkyl, and phenyl, and R' is a member selected from the group consisting of CH$_3$ and CF$_3$.
2. A diamine according to claim 1, wherein R is hydrogen.
3. A diamine according to claim 1, wherein R is a butyl group.
4. A diamine according to claim 1, wherein R is a phenyl group.

* * * * *